United States Patent [19]

Wallner

[11] 4,455,864
[45] Jun. 26, 1984

[54] MEMBRANE OSMOMETER

[76] Inventor: Franz Wallner, Humboldstrasse 22, Berlin 33, Fed. Rep. of Germany

[21] Appl. No.: 349,834

[22] Filed: Feb. 18, 1982

[30] Foreign Application Priority Data

Mar. 17, 1981 [DE] Fed. Rep. of Germany ....... 3110183

[51] Int. Cl.³ .............................................. G01N 13/04
[52] U.S. Cl. ..................................... 73/64.3; 277/117; 277/110
[58] Field of Search .................. 73/64.3; 277/117, 118, 277/110, 111, 177

[56] References Cited

U.S. PATENT DOCUMENTS

| | | | |
|---|---|---|---|
| 2,755,111 | 7/1956 | Newell et al. | 277/110 |
| 3,518,875 | 7/1970 | Charmasson | 73/64.3 |
| 3,590,634 | 7/1971 | Pasternak et al. | 73/64.3 X |
| 3,635,075 | 1/1972 | Gilbert | 73/64.3 |
| 4,006,639 | 2/1977 | Wetterhorn | 73/715 X |
| 4,137,756 | 2/1979 | Cossack et al. | 73/64.3 |
| 4,170,895 | 10/1979 | Kilger | 73/64.3 |

OTHER PUBLICATIONS

"A Foil Swelling Pressure Osmometer", Bertil Eroksson, Chemical Scripts (1971) I, No. 5, pp. 221-226.

Primary Examiner—S. Clement Swisher
Assistant Examiner—Tom Noland
Attorney, Agent, or Firm—Ralf H. Siegemund

[57] ABSTRACT

This invention is directed to a membrane osmometer for direct measurement of osmotic pressures comprising a pressure measuring chamber for receiving pure solvent, a sample chamber separated therefrom for receiving solution to be tested, and a semi-permeable membrane contacting a support plate coarsely pervious to liquids, the membrane being located on the side of the support plate adjacent to the sample chamber, wherein the sample chamber comprises, on its surface nearest the membrane, a conical annular surface which, when the sample chamber and pressure measuring chamber are assembled, presses an elastic sealing ring against both the surface of the membrane facing the sample chamber and against an inner surface of the pressure measuring chamber.

15 Claims, 1 Drawing Figure

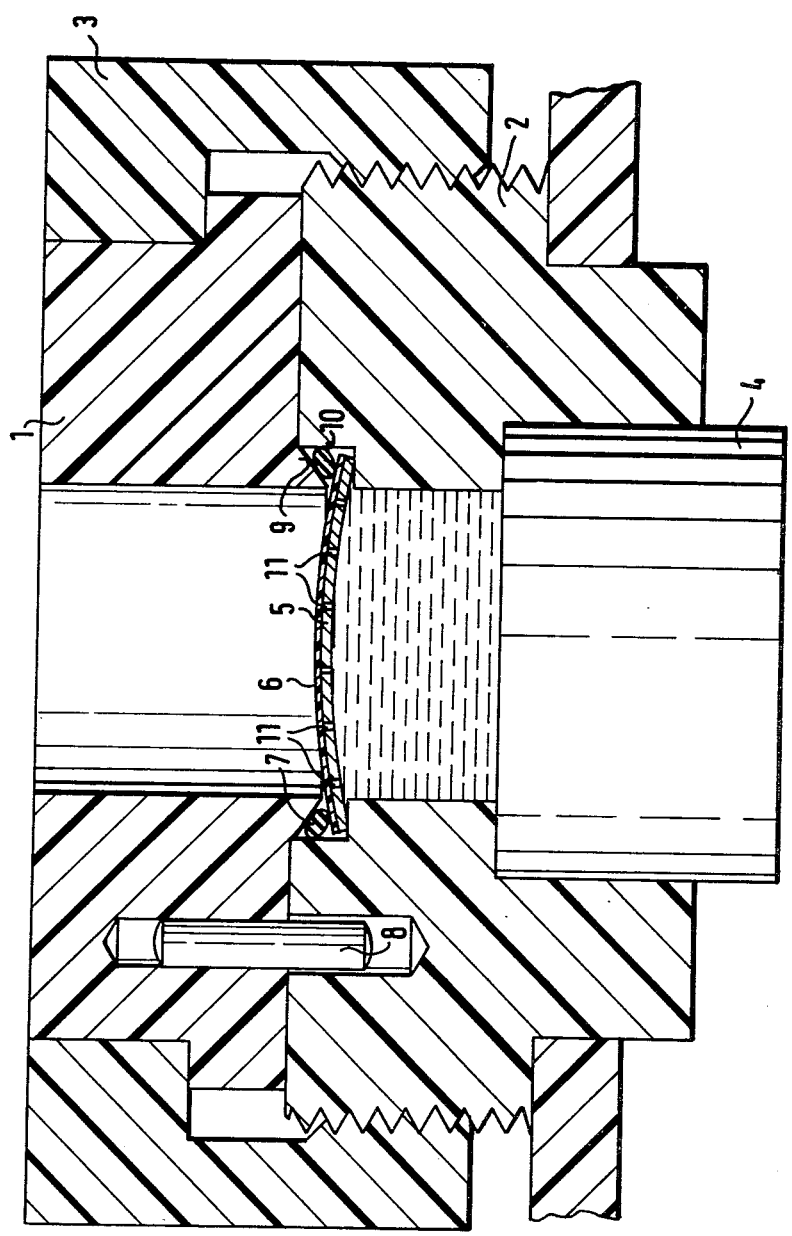

MEMBRANE OSMOMETER

FIELD OF THE INVENTION

This invention relates to a membrane osmometer. More particularly, this invention relates to a membrane osmometer for directly measuring osmotic pressures.

BACKGROUND OF THE INVENTION

Membrane osmometers are used for measuring the osmotic pressure exerted by a solution, i.e., a test liquid, on its solvent. One important field of use for membrane osmometers is the measurement of the colloid osmotic pressure of blood, serum, plasma, or other body fluids in comparison to isotonic saline solution.

It is known for the sample chamber, or the cavity formed to receive the test liquid from the sample chamber, to be left open to the atmosphere. It is also known to support the semi-permeable membrane which separates the pressure measuring chamber from the sample chamber or separates the cavities formed by these chambers from one another, by means of a support or sieve plate which is coarsely pervious to liquids, this plate being provided on the pressure measuring chamber side of the membrane to provide rigid fixing for the generally soft, thin membrane. It is also known to use one or more sealing rings, e.g., O-rings, for sealing the pressure measuring chamber and the membrane which closes it off from the sample chamber or from the atmosphere. It is further known to give the support plate a convex curvature directed towards the sample chamber to promote contact or abutment of the membrane on the support plate even if there is no osmotic differential pressure.

For the purpose of holding the sample chamber and pressure measuring chamber together, typically a screw ring which is fitted, as a screw cap, over one of the chambers and engages an external thread on the other chamber, is used.

Semi-permeable membranes are generally water-permeable, to a greater or lesser extent, both at right angles to the surface of the membrane and also parallel thereto. In socalled asymmetrical membranes, the semi-permeable layer (from about 0.1 to 10 $\mu$m thick) is only a thin surface coating of the membrane structure; the rest of the cross-section of the membrane (from about 30 to 100 $\mu$m thick) is a support structure and is deliberately highly water-permeable in all directions. The semi-permeable layer is generally arranged nearest the sample chamber to facilitate rinsing and cleaning by the test liquid and to prevent, for example, proteins from being trapped in the support fabric of the membrane.

The sealing of the pressure measuring chamber, which is particularly important to the operation of the osmometer, must therefore be effected between the top of the membrane—near its outer edge—and the pressure measuring chamber. Other arrangements for the seal are unsatisfactory or impractical. To ensure maximum stability of volume of the pressure measuring chamber, on which both the duration of measurement and also the accuracy of measurement depend, particularly when the test samples are small, it is important that the membrane is already fitted as tightly as possible against the support plate at the start of measurement. Therefore, it is not enough simply to shape the membrane over the more or less convex support plate by pressing substantially at right angles to the surface of the membrane when the sample chamber and pressure measuring chamber are fitted together; rather, if possible, tension should be produced parallel to the surface of the membrane, towards the edge thereof.

OBJECTS OF THE INVENTION

It is an object of the invention to provide a novel membrane osmometer means.

It is also an object of the invention to provide a membrane osmometer means whereby a single sealing ring performs four functons when the sample chamber and pressure measuring chamber are fitted together, which functions are as follows:

(1) effecting a seal at the surface of the membrane facing the sample chamber;
(2) sealing off the pressure measuring chamber;
(3) stretching the membrane outwards in the direction of the membrane surface; and
(4) sealing the sample chamber to prevent the test liquid from running out.

It is a further object of the invention to provide a membrane osmometer for directly measuring osmotic pressures which has a pressure measuring chamber for receiving a pure solvent, a sample chamber for receiving the test solution which is separated from the pressure measuring chamber and preferably is open to the atmosphere, and a semi-permeable membrane contacting a support plate highly pervious to liquids, said membrane being located on the side of the support plate adjacent to the sample chamber, wherein the wall of the sample chamber comprises on its side nearest the membrane a conelike annular surface which, when the sample chamber and pressure measuring chamber are assembled, presses an elastic sealing ring against the surface of the membrane facing the sample chamber and also against the inner surface of the pressure measuring chamber.

These and other objects of the invention will become more apparent in the discussion below.

BRIEF DESCRIPTION OF THE DRAWING

The FIGURE represents a embodiment of the membrane osmometer according to the invention.

DETAILED DESCRIPTION OF THE INVENTION

Applicant has developed a membrane osmometer which achieves the objects expressed above. According to Applicant's invention, a membrane osmometer for the direct measurement of osmotic pressures has a pressure measuring chamber for receiving pure solvent, a sample chamber for receiving solution to be tested, which is separated from the pressure measuring chamber and is preferably open to the atmosphere, and a semi-permeable membrane contacting a support plate that is highly pervious to liquids, the membrane being located on the side of the support plate adjacent to the sample chamber. Moreover, the sample chamber comprises, on its side nearest the membrane, a conical or cone-like annular surface which, when the sample chamber and pressure measuring chamber are assembled presses an elastic sealing ring against the surface of the membrane facing the sample chamber and also against a preferably cylindrical inner surface of the pressure measuring chamber.

In one embodiment of the invention, the support plate on which the semi-permeable membrane rests and over whose surface it is stretched when the screw ring is tightened, is produced, in known manner, from sheet metal perforated by deep etching, and according to the invention, it is made convex by cold forming. The shaping of the convexity by cold forming (drawing) is substantially simpler and cheaper than the production of a solid component, e.g., by turning and milling or drilling. In addition, a major advantage of the admittedly convex but nevertheless very thin support plate, in terms of the operation of the osmometer, is that, when the apparatus is assembled, the risk of trapping air bubbles in the pressure measuring chamber is substantially less than is the case with the known solid, convex support plates, since the length of the channels in which bubbles can travel up out of the pressure chamber is minimal in the case of the perforated support plate domed according to the invention.

In another embodiment of the osmometer, the support plate mentioned is made of a grade of steel which is not only stainless but also ferromagnetic. This provides the possibility of removing the support plate together with the semipermeable membrane and the sealing ring from the pressure measuring chamber by means of a small magnet. Such removal is necessary because of the arrangement of the cylindrical annular surface according to the invention, on which the sealing ring rests, in the pressure measuring chamber. Since the membrane has to be changed relatively frequently, this option makes operation significantly easier.

The advantages of the arrangement according to the invention are that the functions (1) to (4) mentioned above are performed solely by the operation of tightening the screw ring or fitting the sample chamber and pressure measuring chamber together, without having to make any particularly great demands of the machining tolerances of the components involved. One feature particularly worth noting is the great tightness of the seal between the surface of the membrane and the pressure measuring chamber, and this is of essential importance in the measurement. A further advantage is that, in the arrangement according to the invention, the inclusion of small air bubbles under the support plate and under the sealing ring can easily be prevented, and this again increases the reliability of the measurements and makes it easier, even for inexperienced users, to assemble the osmometer correctly after the semi-permeable membrane has been changed.

The invention can perhaps be better appreciated by making reference to the FIGURE. According to the FIGURE, pressure measuring chamber 2 in which the pressure transducer 4 is tightly fitted is secured to sample chamber 1 by screw ring 3. One or more fitting pins 8 prevent the sample chamber from rotating relative to the pressure measuring chamber when the screw ring is tightened. The pressure measuring chamber cavity inside the pressure measuring chamber 2, which cavity must be filled with solvent free from bubbles of gas, is separated from the outwardly open space in the sample chamber 1, into which the test liquid is introduced, by semi-permeable membrane 6. Support plate 5 ensures that the soft membrane does not bend under the osmotic pressure differential that occurs in operation.

The conical or cone-like surface 9 of the sample chamber 1, together with sealing ring 7, performs functions (1) to (4) mentioned above when the screw ring 3 is tightened. The functions critical to correct measurement of osmotic pressure are functions (1) to (3), namely the stretching of the membrane outwards to reduce the compliance of volume of the pressure measuring chamber, providing a seal between the surface of the membrane and the cylindrical annular surface 10 of the wall of the pressure measuring chamber 2, and sealing off the pressure measuring chamber. Very great demands are made of these seals in terms of their tightness. The sealing function (4) between the top of the membrane and the conical annular surface 9 of the test chamber 1 merely prevents the test liquid from running out.

The perforations 11 are produced by, for example, deep etching in the support plate 5, which, after being etched, is made convex by cold forming. These perforations are only as long as the support plate is thick. Consequently, the danger of air bubbles remaining in one of the perforations during assembly is remote. Any bubbles which do remain are easily visible from above, even if the (more or less transparent) membrane is already in position on the support plate.

The surface 10 of the pressure measuring chamber 2, drawn over the abutment surface of the support plate, ensures that the support plate 5, membrane 6, and sealing ring 7 are totally covered by the solvent before and during assembly of the osmometer. In this way, the inclusion of air bubbles underneath these components is reliably prevented.

The construction of the membrane osmometer according to the invention is intended to promote the use of such equipment particularly in clinical practice, by simplifying the maintenance and operation of the equipment, speeding up the measuring process, and eliminating sources of error.

As mentioned above, the support plate can be comprised of a metal such as stainless steel or sheet metal. The other parts of the sample chamber are comprised of rigid materials such as steel, preferably stainless steel, or a suitable polymeric material. The membrane and the elastic O-ring will be comprised of a suitable flexible polymeric material such as cellulose acetate (membrane) and silicone rubber (O-ring).

The parts can be dimensioned such that the chamber cavity is from 0.4 to 10.0 cm wide and from about 0.5 to 10.0 cm deep, the exterior diameter of the chamber means being from about 2 to 5 cm. The choice of the dimensions of the parts used as well as the relative proportions is well within the skill of the artisan.

The preceding specific embodiments are illustrative of the practice of the invention. It is to be understood, however, that other expedients known to those skilled in the art or disclosed herein, may be employed without departing from the spirit of the invention or the scope of the appended claims.

I claim:

1. A membrane osmometer for direct measurement of osmotic pressures comprising a pressure measuring chamber for receiving pure solvent, a sample chamber separated therefrom for receiving solution to be tested, and a semi-permeable membrane contacting a support plate coarsely pervious to liquids, the membrane being located on the side of the support plate adjacent to the sample chamber, the improvement comprising, the sample chamber including, on its surface nearest the membrane, a conically tapered annular surface oriented so that the tip of a hypothetical cone which surface includes said conical annular surface, is on the side of the membrane opposite the sample chamber, said tapered annular surface, when the sample chamber and pressure measuring chamber are assembled, presses an elastic sealing ring against the surface of the membrane facing the sample chamber and against an inner surface of the pressure measuring chamber.

2. The membrane osmometer of claim 1, wherein the sample chamber is open to the atmosphere.

3. The membrane osmometer of claim 1, wherein the sealing ring has a circular cross-section.

4. The membrane osmometer of claim 1, wherein the inner surface of the pressure measuring chamber is cylindrical.

5. The membrane osmometer of claim 1, wherein the support plate is convexly curved towards the sample chamber.

6. The membrane osmometer of claim 5, wherein the convex curvature results from cold forming.

7. The membrane osmometer of claim 1, wherein the support plate is comprised of sheet metal.

8. The membrane osmometer of claim 7, wherein the support plate is comprised of stainless steel.

9. The membrane osmometer of claim 7, wherein the support plate is comprised of a ferromagnetic alloy.

10. The membrane osmometer of claim 1, wherein the support plate comprises perforations resulting from deep etching.

11. The membrane osmometer of claim 1, wherein the external diameter of the sealing ring in an undeformed state is slightly smaller than the diameter of the inner surface of the pressure measuring chamber.

12. The membrane osmometer of claim 1, wherein the sample chamber and the pressure measuring chamber are held together by a screw ring.

13. The membrane osmometer of claim 12, wherein the screw ring is mounted concentrically with the conical surface of the sample chamber and the inner surface of the pressure measuring chamber.

14. The membrane osmometer of claim 1, wherein the sample chamber and pressure measuring chamber are connected to each other by means of fitting pins and corresponding bores.

15. A membrane osmometer for direct measurement of osmotic pressures comprising a cylindrical pressure measuring chamber for receiving pure solvent, a cylindrical sample chamber for receiving solution to be tested, which sample chamber is positioned immediately over and separated from the pressure measuring chamber, and a semi-permeable membrane contacting a support plate convexly curved toward the sample chamber and coarsely previous to liquids, wherein the support plate is positioned between the measuring chamber and the sample chamber by a recess in the inner surface of the pressure measuring chamber, the sample chamber being open to the atmosphere, the improvement comprising, said sample chamber at its surface nearest to the membrane including a conically tapered annular surface oriented, so that the tip of a hypothetical cone which surface includes said conical annular surface, is on the side of the membrane opposite the sample chamber, said tapered annular surface presses an elastic ring having a circular cross-section against the surface of the membrane facing the sample chamber and against the recessed inner surface of the pressure measuring chamber to seal the top of the pressure measuring chamber, to effect a seal between the membrane and the bottom of the sample chamber, and to stretch the membrane in radial direction.

* * * * *